United States Patent
Yeung et al.

(10) Patent No.: US 9,556,162 B2
(45) Date of Patent: Jan. 31, 2017

(54) COMPOUND FOR THE TREATMENT OF HEPATITIS C

(71) Applicant: Bristol-Myers Squibb Company, Princeton, NJ (US)

(72) Inventors: Kap-Sun Yeung, Madison, CT (US); Katharine A. Grant-Young, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/103,206

(22) PCT Filed: Dec. 8, 2014

(86) PCT No.: PCT/US2014/069052
§ 371 (c)(1),
(2) Date: Jun. 9, 2016

(87) PCT Pub. No.: WO2015/088958
PCT Pub. Date: Jun. 18, 2015

(65) Prior Publication Data
US 2016/0318912 A1    Nov. 3, 2016

Related U.S. Application Data

(60) Provisional application No. 61/915,816, filed on Dec. 13, 2013.

(51) Int. Cl.
*C07D 413/12* (2006.01)

(52) U.S. Cl.
CPC ................... *C07D 413/12* (2013.01)

(58) Field of Classification Search
CPC .................................... C07D 413/12
See application file for complete search history.

(56) References Cited

U.S. PATENT DOCUMENTS 8,048,887 B2    11/2011    Yeung et al.

FOREIGN PATENT DOCUMENTS

| WO | WO 2004/041201 A2 | 5/2004 | |
|---|---|---|---|
| WO | WO 2004041201 A2 * | 5/2004 | ........... C07D 307/84 |
| WO | WO 2010030592 A1 * | 3/2010 | ........... C07D 307/84 |

OTHER PUBLICATIONS

International Search Report for international application No. PCT/US14/069052, issued Jun. 18, 2015.*

* cited by examiner

*Primary Examiner* — Matthew Coughlin
(74) *Attorney, Agent, or Firm* — James Epperson

(57) ABSTRACT

The present invention provides (R)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide (formula I), including pharmaceutically acceptable salts, as well as compositions and methods of using the compound. The compound has activity against hepatitis C virus (HCV) and may be useful in treating those infected with HCV.

3 Claims, No Drawings

COMPOUND FOR THE TREATMENT OF HEPATITIS C

CROSS-REFERENCE TO RELATED APPLICATIONS

This application claims priority to Provisional Patent Application U.S. Ser. No. 61/915,816 filed Dec. 13, 2013, hereby incorporated by reference in its entirety.

BACKGROUND OF THE INVENTION

The disclosure generally relates to the novel compound (R)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide which has activity against hepatitis C virus (HCV) and is useful in treating those infected with HCV. The disclosure also relates to compositions and methods of using this and related compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during exteneded dosing of the combination regimens. U.S. Pat. No. 7,265,152 and the corresponding PCT patent application WO2004/041201 describe compounds of the HCV-796 class. Other compounds have been disclosed, see for example, WO2009/101022.

The invention provides technical advantages, for example, the compound is novel and effective against hepatitis C. Additionally, the compound provides advantages for pharmaceutical uses, for example, with regard to one or more of their mechanism of action, binding, inhibition efficacy, target selectivity, solubility, safety profiles, or bioavailability.

DESCRIPTION OF THE INVENTION

The present invention generally relates to (R)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide having the Formula I, isomers, pharmaceutically acceptable salts, pharmaceutical formulations, and its use in treating hepatitis C.

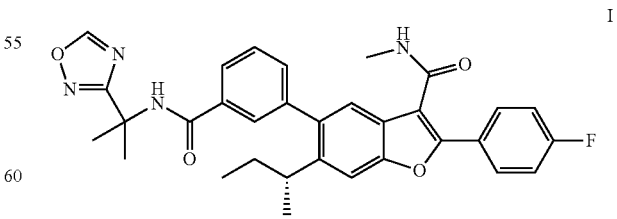

I

One aspect of the invention is the compound of formula I: (R)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide.

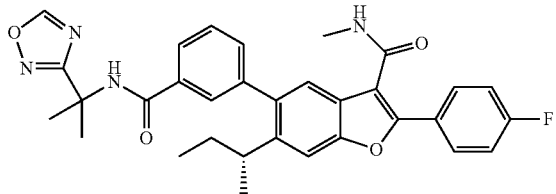

Another aspect of the invention is the compound (S)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide.

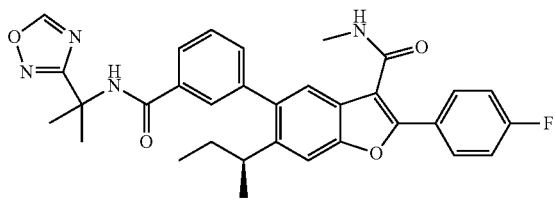 [SMILES: CC[C@H](C)c1cc2oc(-c3ccc(F)cc3)c(C(=O)NC)c2cc1-c1cccc(C(=O)NC(C)(C)c2ncon2)c1]

Another aspect of the invention is the compound 5-(3-((2-(1,2,4-Oxadiazol-3-yl)propan-2-yl)carbamoyl)phenyl)-6-(sec-butyl)-2-(4-fluorophenyl)-N-methylbenzofuran-3-carboxamide.

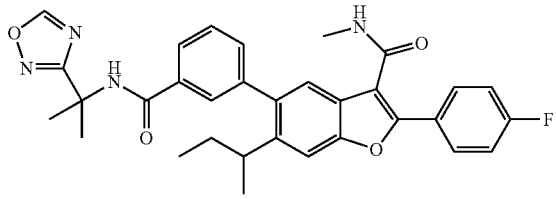 [SMILES: CCC(C)c1cc2oc(-c3ccc(F)cc3)c(C(=O)NC)c2cc1-c1cccc(C(=O)NC(C)(C)c2ncon2)c1]

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucuronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, Remington's Pharmaceutical Sciences, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |

TABLE 1-continued

| Brand Name | Physiological Class | Type of Inhibitor or Target | Source Company |
|---|---|---|---|
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immuno-modulator | immune modulator | Maxim Pharmaceuticals Inc., San Diego, CA |
| CellCept | Immuno-suppressant | HCV IgG immuno-suppressant | F. Hoffmann-La Roche LTD, Basel, Switzerland |
| Civacir | Immuno-suppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |

TABLE 1-continued

| Brand Name | Physiological Class | Type of Inhibitor or Target | Source Company |
|---|---|---|---|
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Gilead (formerly from Pharmasset) |
| PSI-7977 sofosbuvir | Antiviral | Nucleotide NS5B Polymerase Inhibitor | Gilead (formerly from Pharmasset) |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |
| asunaprevir | Antiviral | serine protease inhibitor | Bristol-Myers Squibb |
| BMS-791325 | Antiviral | NS5B Polymerase Inhibitor | Bristol-Myers Squibb |
| daclatasvir | Antiviral | HCV NS5A replication complex inhibitor | Bristol-Myers Squibb |
| GS-5885 | Antiviral | HCV NS5A replication complex inhibitor | Gilead |

Synthetic Methods

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" or "RT" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine; TEA for triethylamine; DCM for dichloromethane Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "atm" for atmosphere, "psi" for pounds per square inch, "conc." for concentrate, "sat" or "sat'd "for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

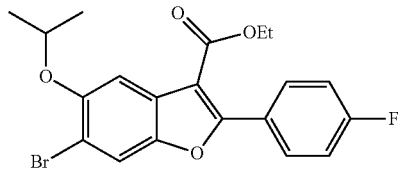 [SMILES: CCOC(=O)c1c(-c2ccc(F)cc2)oc2cc(Br)c(OC(C)C)cc12]

Ethyl 6-bromo-2-(4-fluorophenyl)-5-isopropoxybenzofuran-3-carboxylate

N-Bromosuccinimide (624 mg, 3.51 mmol) was added to a solution of ethyl 2-(4-fluorophenyl)-5-isopropoxybenzofuran-3-carboxylate (1000 mg, 2.92 mmol, prepared in a similar manner as described in WO2004/041201) in acetonitrile (100 mL). The mixture was stirred at room temperature for 19 hrs. The solvent was removed and the residue was purified by Biotage column chromatography (Biotage 25s silica gel column, CH$_2$Cl$_2$/Hexane=0 to 20%) to give 764 mg (62%) of the target compound. $^1$H NMR (500 MHz, CHLOROFORM-d) δ 8.05 (dd, J=8.9, 5.4 Hz, 2H), 7.75 (s, 1H), 7.64 (s, 1H), 7.20 (t, J=8.7 Hz, 2H), 4.45-4.45 (m, 1H), 4.42 (q, J=7.1 Hz, 2H), 1.53-1.36 (m, 9H). LCMS Rt (retention time)=4.545 min., m/z 421, 423 (M+H). The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

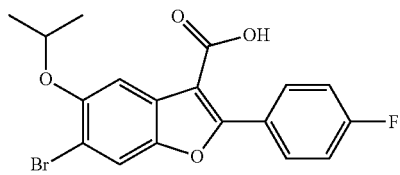 [SMILES: CC(C)Oc1cc2c(C(=O)O)c(-c3ccc(F)cc3)oc2cc1Br]

6-Bromo-2-(4-fluorophenyl)-5-isopropoxybenzofuran-3-carboxylic acid. A 1M solution of sodium hydroxide (24.21 mL, 24.21 mmol) was added into a solution of ethyl 6-bromo-2-(4-fluorophenyl)-5-isopropoxybenzofuran-3-carboxylate (3.4 g, 8.07 mmol) in 1:1 MeOH (34 mL)/THF (34 mL). The mixture was stirred with gentle heating at 40° C. overnight. The mixture was cooled to 0° C. and ice-cold 1M HCl (100 mL) was added. The resulting yellow solid was filtered, washed with water and dried under vacuum for three days. An amount of 3.137 g (99%) of 6-bromo-2-(4-fluorophenyl)-5-isopropoxybenzofuran-3-carboxylic acid was obtained. $^1$H NMR (400 MHz, DMSO-d$_6$) δ 8.10-8.03 (m, 3H), 7.63 (s, 1H), 7.45-7.37 (m, 2H), 4.69-4.61 (m, 1H), 1.36 (d, J=6.0 Hz, 6H). LCMS Rt=3.77 min., m/z 393 (M+1), 92.7% purity. The LC/MS data was obtained on a Shimadzu analytical LC/Micromass Platform LC (ESI+) at 220 nm using the following set of conditions: Phenomenex Luna 3 m C18, 2×50 mm column, with a gradient of 0-100% B (B=90% HPLC grade acetonitrile/0.1% trifluoroacetic acid/10% HPLC grade water), (A=90% HPLC grade water/ 0.1% trifluoroacetic acid/10% HPLC grade acetonitrile), in 4 minutes with a 1 minute hold at a rate of 0.8 mL/minute.

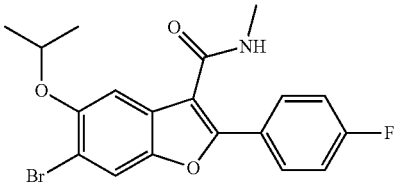 [SMILES: CNC(=O)c1c(-c2ccc(F)cc2)oc2cc(Br)c(OC(C)C)cc12]

6-Bromo-2-(4-fluorophenyl)-5-isopropoxy-N-methylbenzofuran-3-carboxamide

HATU (4.85 g, 12.76 mmol) was added to a mixture of 6-bromo-2-(4-fluorophenyl)-5-isopropoxybenzofuran-3-carboxylic acid (3.137 g, 7.98 mmol), methylamine hydrochloride (0.808 g, 11.97 mmol), and N,N-diisopropylethylamine (6.95 mL, 39.9 mmol) in DMF (50 mL). The reaction mixture was stirred at room temperature for 2 hrs. Ice-water (200 g) was then added to the mixture. The solid was filtered, washed with water and dried to give 6-bromo-2-(4-fluorophenyl)-5-isopropoxy-N-methylbenzofuran-3-carboxamide (3.175 g, 98%). $^1$H NMR (400 MHz, CHLOROFORM-d) δ 7.90-7.83 (m, 2H), 7.73 (s, 1H), 7.43 (s, 1H), 7.25-7.18 (m, 2H), 5.79 (br. s., 1H), 4.63 (dt, J=12.2, 6.1 Hz, 1H), 3.00 (d, J=5.0 Hz, 3H), 1.43 (d, J=6.0 Hz, 6H). LCMS Rt=3.571 min., m/z 407 (M+1), 97.77% purity. The LC/MS data was obtained on a Shimadzu analytical LC/Micromass Platform LC (ESI+) at 220 nm using The following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

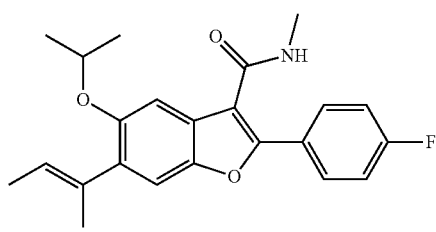 [SMILES: C/C=C(\C)c1cc2oc(-c3ccc(F)cc3)c(C(=O)NC)c2cc1OC(C)C]

(E)-6-(But-2-en-2-yl)-2-(4-fluorophenyl)-5-isopropoxy-N-methylbenzofuran-3-carboxamide A mixture of 6-bromo-2-(4-fluorophenyl)-5-isopropoxy-N-methylbenzofuran-3-carboxamide (1000 mg, 2.462 mmol), toluene (100 mL), water (33.3 mL), cesium carbonate (3609 mg, 11.08 mmol), potassium (Z)-but-2-en-2-yltrifluoroborate (598 mg, 3.69 mmol), and 1,1'-bis(diphenylphosphino)ferrocenepalladium(II) dichloride (203 mg, 0.246 mmol) was de-gassed/flushed with nitrogen over 15 minutes, and then heated for 10 hrs at 90° C. LCMS analysis indicated the starting material was consumed. The reaction mixture was cooled to room temperature, diluted with EtOAc (300 mL), and then washed with water and brine, dried over MgSO$_4$ and filtered. The filtrate was concentrated to give a residue. The residue was purified by Biotage column chromatography (Biotage 40 m silica gel column, EtOAc/Hexane=0 to 40%) to give the product (829 mg, 88%) as a white solid. 1H NMR (DMSO-d$_6$, 500 MHz): δ ppm 8.36 (q, J=4.4 Hz, 1H), 7.93 (t, J=6.6 Hz, 2H), 7.30-7.39 (m, 3H), 7.07 (s, 1H), 5.51-5.58 (m, 1H), 4.59 (dt, J=12.1, 6.0 Hz, 1H), 2.84 (d, J=4.6 Hz, 3H), 1.97 (s, 3H), 1.74 (d, J=6.7 Hz, 3H), 1.29 (d, J=6.0 Hz, 6H). $^{13}$C NMR (DMSO-d$_6$, 126 MHz): δ ppm=164.0, 162.0, 152.5, 152.0, 148.0, 136.0, 135.2, 129.7, 129.6, 126.8, 126.6, 126.5, 124.3, 116.4, 116.2, 114.3, 111.8, 105.2, 71.0, 26.6, 22.3, 17.5, 14.3. Strong NOE between the benzofuran C7 proton and the vinyl proton was observed in NMR experiments which supported the product as the E-isomer. LCMS Rt=2.085 min., m/z 382.3 (M+H). The LC/MS data was obtained on a Shimadzu analytical LCMS (ESI+) at 220 nm using the following set of conditions: Phenomenex Luna 3 m C18, 2×30 mm column, with a gradient of 0-100% B (B=90% HPLC grade acetonitrile/0.1% trifluoroacetic acid/ 10% HPLC grade water), (A=90% HPLC grade water/0.1% trifluoroacetic acid/10% HPLC grade acetonitrile), in 2 minutes with a 1 minute hold at a rate of 1 mL/minute.

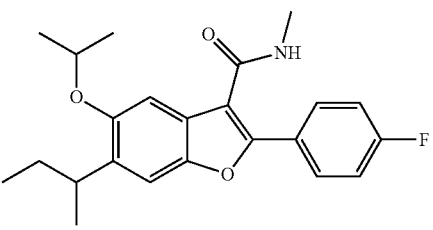 [SMILES: CCC(C)c1cc2oc(-c3ccc(F)cc3)c(C(=O)NC)c2cc1OC(C)C]

6-(sec-Butyl)-2-(4-fluorophenyl)-5-isopropoxy-N-methylbenzofuran-3-carboxamide

To a round bottom flask was added (E)-6-(but-2-en-2-yl)-2-(4-fluorophenyl)-5-isopropoxy-N-methylbenzofuran-3-carboxamide (1.4 g, 3.67 mmol) in ethanol (125 ml). The solution was de-gassed, flushed with nitrogen over 10 minutes then 0.1 eq of 10% palladium on carbon was added. The flask was fitted with a balloon of hydrogen and the mixture stirred overnight at room temperature. The crude product was pushed through a plug of celite/magnesium sulfate, in a syringe filter, then evaporated to dryness to give a quantitative yield of 6-(sec-butyl)-2-(4-fluorophenyl)-5-isopropoxy-N-methylbenzofuran-3-carboxamide. $^1$H NMR (500 MHz, DMSO-d$_6$) δ ppm 8.37 (m, 1H), 7.90-7.97 (m, 2H), 7.45 (s, 1H), 7.34-7.40 (m, 2H), 7.09 (s, 1H), 4.63 (m, 1H), 3.16 (m, 1H), 2.84 (d, J=4.73 Hz, 3H), 1.54-1.68 (m, 2H), 1.32 (d, J=5.99 Hz, 6H), 1.19-1.22 (m, 3H), 0.81 (t, J=7.41 Hz, 3H). LCMS Rt=3.973 min., m/z 384.3 (M+H). The LC/MS data was obtained on a Shimadzu analytical LC/Micromass Platform LC (ESI+) at 220 nm using the following set of conditions: Phenomenex Luna 3 m C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

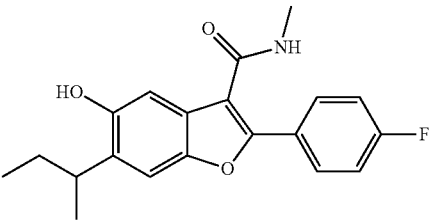 [SMILES: CCC(C)c1cc2oc(-c3ccc(F)cc3)c(C(=O)NC)c2cc1O]

6-(sec-Butyl)-2-(4-fluorophenyl)-5-hydroxy-N-methylbenzofuran-3-carboxamide

Three eq. of a 1M solution of trichloroborane in DCM (dichloromethane) (11.6 ml, 11.6 mmol) was added dropwise to a solution of 6-(sec-butyl)-2-(4-fluorophenyl)-5-isopropoxy-N-methylbenzofuran-3-carboxamide (1.48 g, 3.8 mmol) in DCM (138 ml) at 0° C. for 30 min. The ice bath was removed and the reaction mixture was allowed to warm to rt (room temperature) and stir for 1 hour. Solvent was removed on the rotovap, fresh methanol was added and the process repeated×4. Finally, diethylether was added, the product was evaporated and placed under high vac for 2 hours giving 1.3 g of 6-(sec-butyl)-2-(4-fluorophenyl)-5-hydroxy-N-methylbenzofuran-3-carboxamide (91% yield, 94% purity) as a light yellow solid. $^1$H NMR (500 MHz, DMSO-d$_6$) δ ppm 9.34 (s, 1H), 8.37 (m, 1H), 7.85-7.96 (m, 2H), 7.32-7.39 (m, 3H), 7.00 (s, 1H), 3.08-3.18 (m, 1H), 2.82 (d, J=4.57 Hz, 3H), 1.53-1.71 (m, 2H), 1.19 (d, J=6.94 Hz, 3H), 0.82 (t, J=7.41 Hz, 3H). LCMS Rt=1.795 min., m/z 342.3 (M+H). The LC/MS data was obtained on a Shimadzu analytical LCMS (ESI+) at 220 nm using the following set of conditions: Phenomenex Luna 3 m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

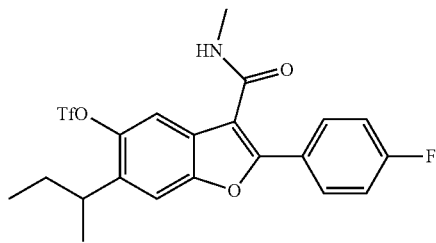 [SMILES: CCC(C)c1cc2oc(-c3ccc(F)cc3)c(C(=O)NC)c2cc1OS(=O)(=O)C(F)(F)F]

6-(sec-Butyl)-2-(4-fluorophenyl)-3-(methylcarbamoyl)benzofuran-5-yl trifluoromethanesulfonate Under nitrogen to 6-(sec-butyl)-2-(4-fluorophenyl)-5-hydroxy-N-methylbenzofuran-3-carboxamide (1.3 g, 3.86 mmol) in DCM (63 mL) was added triethylamine (1.08 ml, 7.71 mmol) at rt. The mixture was cooled to 0° C. and 1,1,1-trifluoro-N-phenyl-N-((trifluoromethyl)sulfonyl)methanesulfonamide (1.65 g, 4.63 mmol) was slowly added portion-wise. The resulting mixture was allowed to warm to rt and stirred for 2 days. An aliquot was removed and LCMS was run to check reaction progress; data suggested a 1:1 mixture of phenolic starting material/product. Another 1.2 eq of 1,1,1-trifluoro-N-phenyl-N-((trifluoromethyl)sulfonyl)methanesulfonamide (1.65 g, 4.63 mmol) was added along with triethylamine (1.08 ml, 7.71 mmol) and the mixture was stirred at rt overnight. The reaction mixture was further diluted with DCM (50 mL), washed with water, brine, dried over magnesium sulfate, filtered and then concentrated to give a tannish/pink solid. The crude material was purified on the Biotage using a normal phase silica gel 220 g Isco column using 0-40% EtOAc/Hexane giving 1.57 g (86% yield) of 6-(sec-butyl)-2-(4-fluorophenyl)-3-(methylcarbamoyl)benzofuran-5-yl trifluoromethanesulfonate as a light yellow/white solid. $^1$H NMR (400 MHz, DMSO-d$_6$) δ ppm 8.47 (m, 1H), 7.91-7.99 (m, 2H), 7.90 (s, 1H), 7.55 (s, 1H), 7.42 (t, J=8.91 Hz, 2H), 2.94-3.04 (m, 1H), 2.82 (d, J=4.52 Hz, 3H), 1.63-1.75 (m, 2H), 1.28 (d, J=6.78 Hz, 3H), 0.80 (t, J=7.28 Hz, 3H). LCMS Rt=2.144 min., m/z 474.15 (M+H). The LC/MS data was obtained on a Shimadzu analytical LCMS (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

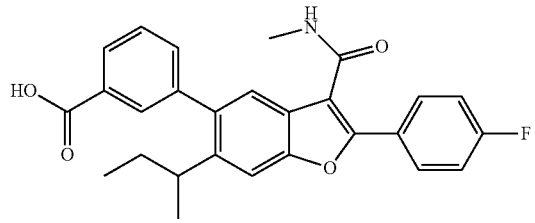 [SMILES: CCC(C)c1cc2oc(-c3ccc(F)cc3)c(C(=O)NC)c2cc1-c1cccc(C(=O)O)c1]

3-(6-(sec-Butyl)-2-(4-fluorophenyl)-3-(methylcarbamoyl)benzofuran-5-yl)benzoic acid To a sealed tube was added 6-(sec-butyl)-2-(4-fluorophenyl)-3-(methylcarbamoyl)benzofuran-5-yl trifluoromethanesulfonate (1.50 g, 3.17 mmol), dioxane (120 ml), water (24 ml), cesium carbonate (3.09 g, 9.51 mmol), 3-boronobenzoic acid (947.5 mg, 5.71 mmol), and palladium tetrakis(triphenylphosphine) (0.634 g, 0.732 mmol). The vessel was sealed, flushed/degassed×3 with nitrogen and heated at 90° C. for 6 hours. The reaction mixture was cooled to 0° C. and added to 200 mL of 0.1M aq HCl along with 100 mL of wet ice. The resulting light tan was filtered, washed with 50 mL water and dried under house vacuum. The resulting solid was washed with 10 mL hexane, then 2×10 mL 10% diethylether/hexane to give a 1.2 g (85% yield) of 3-(6-(sec-butyl)-2-(4-fluorophenyl)-3-(methylcarbamoyl)benzofuran-5-yl)benzoic acid as an off-white/light tan solid. $^1$H NMR (500 MHz, DMSO-d$_6$) δ ppm 12.45-13.50 (br.s., 1H), 8.43 (m, 1H), 7.95-8.04 (m, 3H), 7.87 (s, 1H), 7.71 (s, 1H), 7.53-7.67 (m, 2H), 7.37-7.45 (m, 3H), 2.67-2.85 (m, 4H), 1.51-1.69 (m, 2H), 1.19 (d, J=6.78 Hz, 3H), 0.66 (t, J=7.33 Hz, 3H). LCMS Rt=1.920 min., m/z 446.4 (M+H). The LC/MS data was obtained on a Shimadzu analytical LC/Micromass Platform LC (ESI+) at 220 nm using the following set of conditions: Phenomenex Luna 3 m C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

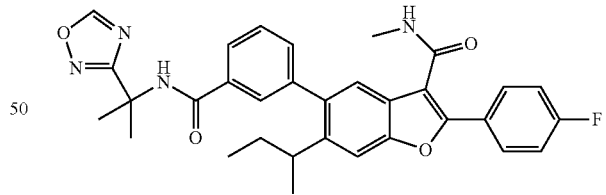

5-(3-((2-(1,2,4-Oxadiazol-3-yl)propan-2-yl)carbamoyl)phenyl)-6-(sec-butyl)-2-(4-fluorophenyl)-N-methylbenzofuran-3-carboxamide To a 500 mL round bottom flask was added 3-(6-(sec-butyl)-2-(4-fluorophenyl)-3-(methylcarbamoyl)benzofuran-5-yl)benzoic acid (1.500 g, 3.37 mmol), DMF (100 mL), N-ethyl-N-isopropylpropan-2-amine (3.52 mL, 20.2 mmol), 2-(1,2,4-oxadiazol-3-yl)propan-2-amine, HCl (1.102 g, 6.73 mmol), and HATU (2-(3H-[1,2,3]triazolo [4,5-b]pyridin-3-yl)-1,1,3,3-tetramethylisouronium hexafluorophosphate(V)) (3.84 g, 10.1 mmol). The flask was sealed and the mixture stirred overnight under nitrogen at room temperature. To the resulting brown solution was added 300 mL of ice water and the solution pH was adjusted to ~7 (with 0.05M HCl). The resulting ivory colored solid was filtered with a fine Buchner funnel and dried under vacuum overnight to give 1.505 g (77% yield, 95% purity). $^1$H NMR (400 MHz, DMSO-d$_6$) δ ppm 9.43 (s, 1H), 8.76 (s, 1H), 8.39-8.48 (m, 1H), 7.98 (m, 2H), 7.87 (d, J=7.78 Hz, 1H), 7.77 (s, 1H), 7.69 (s, 1H), 7.55 (t, J=7.65 Hz, 1H), 7.46 (d, J=7.53 Hz, 1H), 7.35-7.42 (m, 3H), 2.79 (d, J=4.52 Hz, 3H), 2.67-2.76 (m, 1H), 1.69 (s, 6H), 1.48-1.66 (m, 2H), 1.17 (d, J=7.03 Hz, 3H), 0.66 (t, J=7.28 Hz, 3H). LCMS Rt=1.963 min., m/z 555.4 (M+H). The LC/MS data was obtained on a Shimadzu analytical LC/Micromass Platform LC (ESI+) at 220 nm using the following set of conditions: Phenomenex Luna 3 μm C18, 2×30 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

Chiral Separation.

1.668 g of racemic 5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide was separated by Chiral SFC using the following method: A Berger Multigram II prep SFC equipped with a ChiralCel OD-H, 30×250 mm, 5 μm column employing 20% EtOH (w/15 mM NH$_3$)/80% CO$_2$ as mobile phase at 150 bar, 40° C., and a flow rate of 70 mL/min with stop time=15 min and UV detection at a wavelength of 310 nm. Multiple injections were made and stacked (each injection 4.0 mL and ~12 mg/mL in ~1:1 CHCl$_3$:EtOH with fraction collections at 7.95-9.50 min (Rt=8.13 min) to obtain 718.2 mg of Enantiomer 1, and at 9.95-12.50 min (Rt=10.33 min) to obtain 692.8 mg of the desired Enantiomer 2. Enantiomer 1: (S)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide: $[α]^{20}_D$+21.09 (2.75 mg/mL, MeOH), 100% ee (Rt=6.38 min). Enantiomer 2: (R)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide: $[α]^{20}_D$-21.82 (2.75 mg/mL, MeOH), 100% ee (Rt=8.70 min), $^1$H NMR (400 MHz, DMSO-d$_6$) δ ppm 9.43 (s, 1H), 8.75 (s, 1H), 8.44 (m, 1H), 7.98 (m, 2H), 7.87 (d, J=7.78 Hz, 1H), 7.77 (s, 1H), 7.69 (s, 1H), 7.55 (t, J=7.65 Hz, 1H), 7.46 (d, J=7.53 Hz, 1H), 7.34-7.42 (m, 3H), 2.79 (d, J=4.52 Hz, 3H), 2.65-2.75 (m, 1H), 1.69 (s, 6H), 1.49-1.67 (m, 2H), 1.17 (d, J=6.78 Hz, 3H), 0.66 (t, J=7.28 Hz, 3H). The absolute stereochemistry of the benzylic carbon at C6 position of the benzofuran ring was determined as R from an X-ray co-crystal structure of Enantiomer 2 in complex with wild type NS5B 1b enzyme. Optical purity was determined by using a ChiralCel OD-H, 4.6×250 mm, 5 μm column and employing 20% EtOH (w/15 mM NH$_3$)/80% CO$_2$ as mobile phase at 150 bar, 40° C., and a flow rate of 2 mL/min with stop time=12 min and UV detection at a wavelength of 310 nm.

Biological Methods

HCV NS5B RdRp Cloning, Expression, and Purification.

The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The E. coli competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM MgCl$_2$, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, MgCl$_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp enzyme assay. A solution phase activity assay measuring the incorporation of radiolabeled nucleotides using scintillation counting of TCA precipitated product was used to determine inhibitor IC$_{50}$ values. The reaction contains pGpG primer (8.6 μM), homopolymeric C template (0.35 nM), NS5B enzyme (2.8 nM), 20 mM tris-HCL (pH 7.5), 5 mM MgCl$_2$, 2.5 mM KCl, 1 mM DTT, 50 μg/ml BSA (B6917, Sigma), 1 μM cold GTP and [$^{33}$P]-GTP substrate (1 μCi, 3000 Ci/mmol, Amersham, GE Healthcare, Piscataway, N.J.). After a 24 h preincubation of NS5B polymerase, template and compound, primer-dependent RNA synthesis was initiated by the addition of primer and GTP. Reactions were incubated at 30° C. for 15 min. The newly synthesized RNA product was precipitated by 10% TCA and quantified on the Packard Top Count NXT. IC$_{50}$ values for compounds were determined using seven different [I]. IC$_{50}$ values were calculated from the inhibition using the four-parameter logistic formula y=A+((B−A)/(1+((C/x)^D))), where A and B denote minimal and maximal % inhibition, respectively, C is the IC$_{50}$, D is hill slope and x represents compound concentration.

Cell Lines.

The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a Renilla luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 μL at a density of 2.4×10$^3$ cells/well) in DMEM containing 4% FBS (final DMSO concentration at 0.5%). After 3 days incubation at 37 C, cells were analyzed for Renilla Luciferase activity using the EnduRen substrate (Promega cat #E6485) according to the manufacturer's directions. Briefly, the EnduRen substrate was diluted in DMEM and then added to the plates to a final concentration of 7.5 μM. The plates were incubated for at least 1 h at 37° C. then read on a Viewlux Imager (PerkinElmer) using a luminescence program. The 50% effective concentration (EC$_{50}$) was calculated using the four-parameter logistic formula noted above.

To assess cytotoxicity of compounds, Cell Titer-Blue (Promega) was added to the EnduRen-containing plates and incubated for at least 4 h at 37° C. The fluorescence signal from each well was read using a Viewlux Imager. All CC$_{50}$ values were calculated using the four-parameter logistic formula. 1b Replicon and enzyme data for Enantiomer 2 is reported in Table 2.

TABLE 2

| Example | Structure | EC$_{50}$ (μM) | IC$_{50}$ (μM) |
|---|---|---|---|
| Enantiomer 2 | 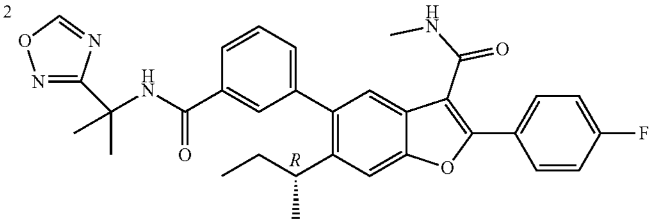 | 0.0055 | 0.0023 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. The compound (R)-5-(3-((2-(1,2,4-oxadiazol-3-yl)propan-2-yl)carbamoyl)phenyl)-6-(sec-butyl)-2-(4-fluorophenyl)-N-methylbenzofuran-3-carboxamide, or a pharmaceutically acceptable salt thereof

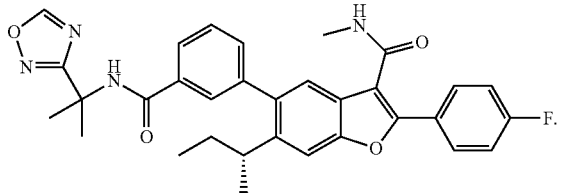 [SMILES: CC[C@@H](C)c1cc2oc(-c3ccc(F)cc3)c(C(=O)NC)c2cc1-c1cccc(C(=O)NC(C)(C)c2ncon2)c1]

2. A composition comprising a compound of claim 1, or a pharmaceutically acceptable salt thereof, and a pharmaceutically acceptable carrier.

3. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 9,556,162 B2
APPLICATION NO. : 15/103206
DATED : January 31, 2017
INVENTOR(S) : Yeung et al.

Page 1 of 1

It is certified that error appears in the above-identified patent and that said Letters Patent is hereby corrected as shown below:

On the Title Page

Item (57) ABSTRACT
Column 2, Line 8:
Below "HCV." insert

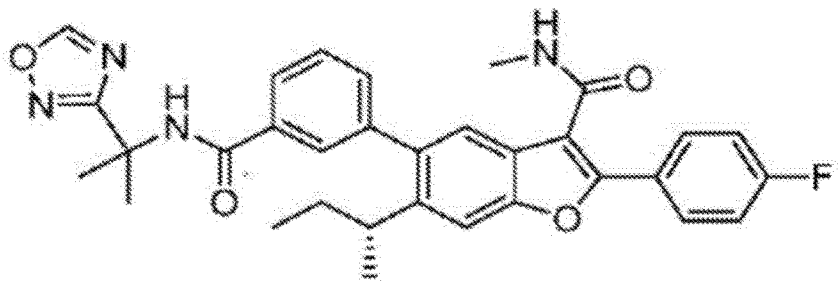

--                                   (I)         --.

Signed and Sealed this
Twenty-fifth Day of September, 2018

Andrei Iancu
*Director of the United States Patent and Trademark Office*